United States Patent [19]
Boudouris et al.

[11] 3,980,855
[45] Sept. 14, 1976

[54] METHOD AND APPARATUS FOR DISSIPATING HIGH FREQUENCY ENERGY INSIDE A MATERIAL TO BE TREATED

[75] Inventors: Georges Boudouris, Grenoble; Gregoire Kalopissis, Paris; Paul Roussopoulos, Paris; Jean-Luc Levesque, Paris, all of France

[73] Assignee: L'Oreal, Paris, France

[22] Filed: Mar. 22, 1973

[21] Appl. No.: 344,048

Related U.S. Application Data

[63] Continuation-in-part of Ser. No. 196,122, Nov. 5, 1971, abandoned.

[52] U.S. Cl. .................. 219/10.55 A; 219/10.55 R; 219/10.55 F; 219/10.55 M; 219/10.81
[51] Int. Cl.² ........................................... H05B 9/06
[58] Field of Search .......... 219/10.51, 10.57, 10.61, 219/10.73, 10.81, 222, 10.55 R, 10.55 A, 10.55 F; 34/1

[56] References Cited
UNITED STATES PATENTS

| | | |
|---|---|---|
| 1,892,106 | 12/1932 | Jancke .............................. 219/222 |
| 2,494,716 | 1/1950 | McMahon et al. .......... 219/10.81 X |
| 2,526,283 | 10/1950 | Schmidt ...................... 219/10.81 X |
| 2,564,675 | 8/1951 | Crook .......................... 219/10.81 X |
| 2,811,624 | 10/1957 | Haagensen .................. 219/10.55 R |
| 2,817,739 | 12/1957 | Haagensen ................... 219/10.55 F |
| 3,668,358 | 6/1972 | Stenstrom .................... 219/10.55 A |
| 3,722,105 | 3/1973 | Martery .................... 219/10.81 UX |
| 3,778,578 | 12/1973 | Loug ............................ 219/10.55 R |

*Primary Examiner*—Bruce A. Reynolds
*Attorney, Agent, or Firm*—Brisebois & Kruger

[57] ABSTRACT

Method and apparatus for dissipating high frequency electromagnetic energy inside a material. The apparatus comprises a conductive jacket defining a resonant chamber, a coil inside said chamber connected to a coaxial cable supplied by a high frequency generator, the frequency of which is equal to the resonant frequency of the chamber. The impedance of the resonator and its contents is matched to that of the coaxial cable. Automatic means may be provided for altering the resonator impedance to compensate for changes in load impedance.

14 Claims, 15 Drawing Figures

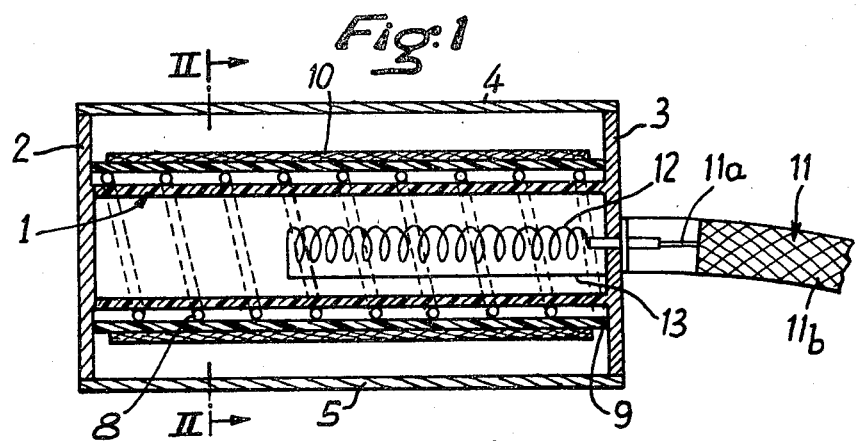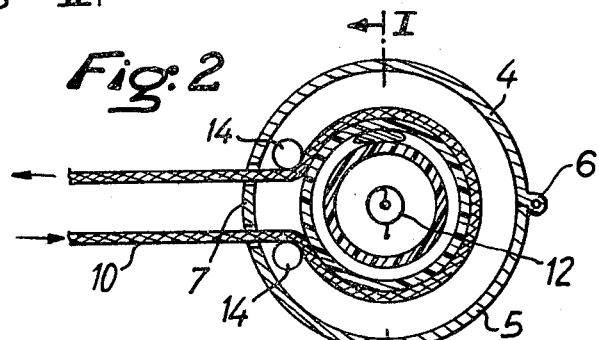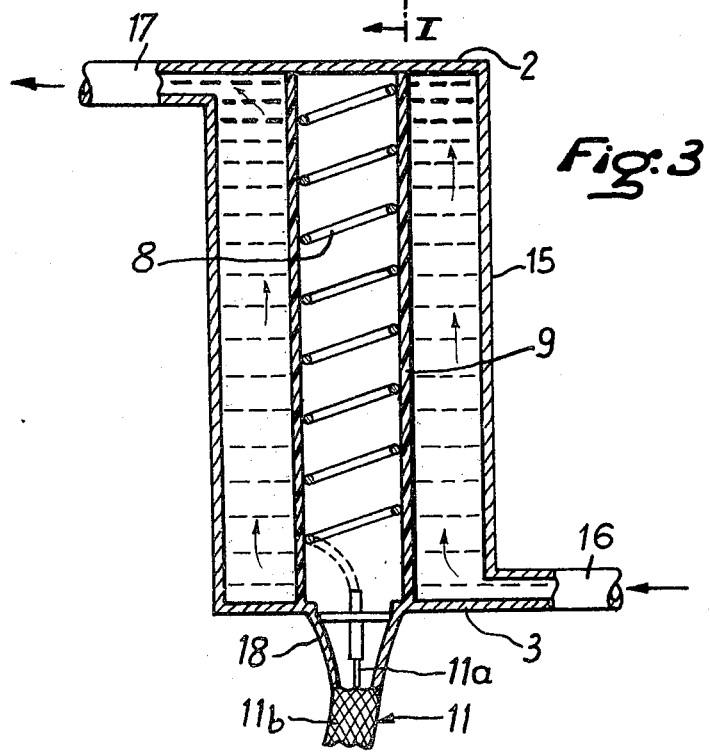

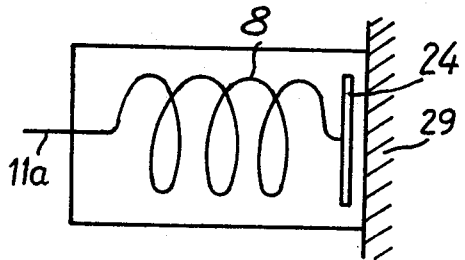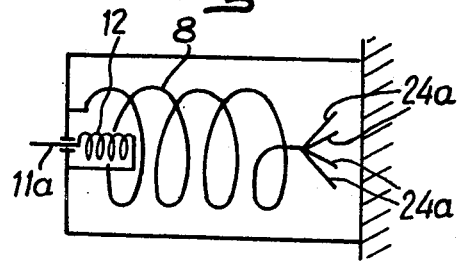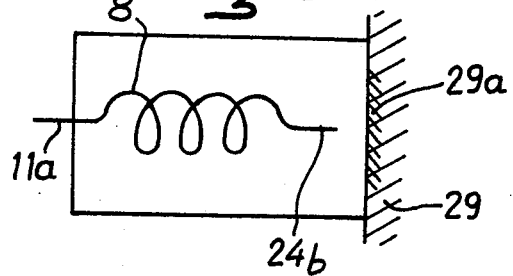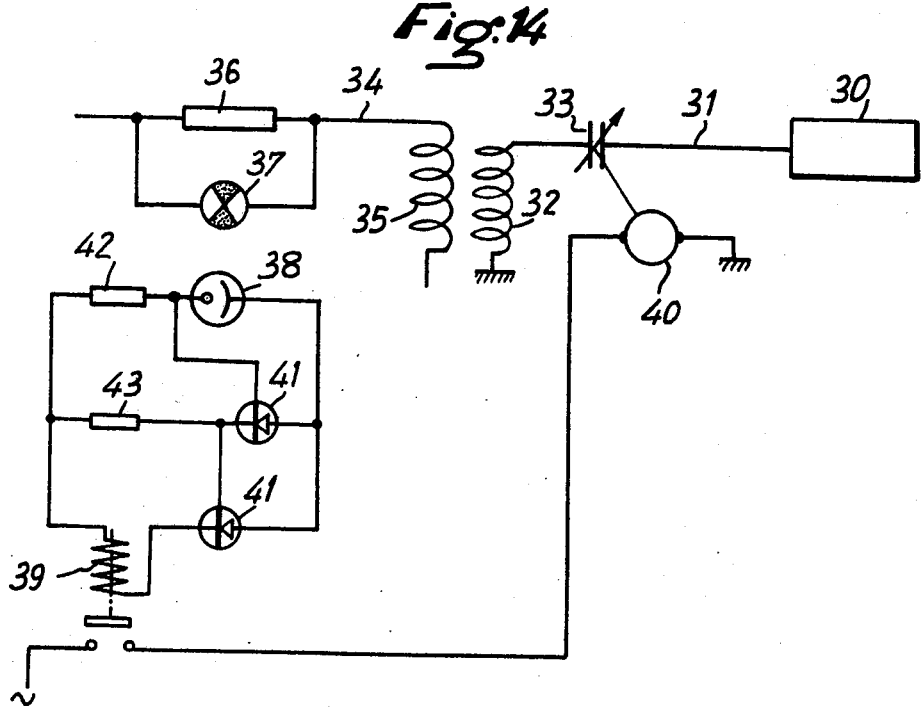

METHOD AND APPARATUS FOR DISSIPATING HIGH FREQUENCY ENERGY INSIDE A MATERIAL TO BE TREATED

SUMMARY OF THE INVENTION

This application is a continuation-in-part of our prior application, Ser. No. 196,122, filed Nov. 5, 1971, now abandoned.

This invention relates to a new method of dissipating high frequency electromagnetic energy inside various materials and to apparatus carrying out this method.

A process has already been suggested for treating hair utilizing dielectric losses which consists in subjecting the hair to a high frequency electromagnetic field by placing it in a resonator matched to the transmission line and the high frequency generator.

As a consequence of recent experiments applicants have discovered that these means for treating the hair, as well as new means which will be described in the present application, may advantageously be used to dissipate high frequency electromagnetic energy inside materials of various types other than hair and analogous fibers.

The present invention also relates to apparatus for carrying out this process.

It is an object of the present invention to provide as a new article of manufacture a device for dissipating high frequency electromagnetic energy inside a material characterized by the fact that it comprises in combination:

a jacket which is closed or substantially closed in the electromagnetic sense of the term, constituting the outer part of a resonator;

a coaxial line connecting said resonator to a generator of electromagnetic energy at a frequency between about 10 and about 2000 megahertz;

FIG. 1a is a view similar to FIG. 1, showing an embodiment in which the jacket is lined with an insulating material.

a helical coil inside the jacket;

means for holding or guiding the material to be treated in the space between the inner surface of the jacket and the exterior of the coil;

the resonator constituted by the jacket, the coil, and the material to be treated, being matched to the transmission line and the high frequency generator.

By a "jacket closed in the electromagnetic sense of the term" is meant an electrically conductive jacket constituting a closed or substantially closed wall, any openings which have dimensions such that they do not permit substantial quantities of electromagnetic energy to pass outward therethrough from the interior of the jacket.

The jacket of the device according to the invention may, for example, be made from several parts so connected to each other that they may be separated to permit the introduction into said jacket of the material to be treated, after which the jacket is closed.

In another embodiment, the jacket may comprise openings having dimensions so small that they do not permit a substantial quantity of high frequency electromagnetic energy to escape but sufficiently large to admit continuously into the jacket a material to be treated, which material may advantageously be in the form of a wire or strip, but may also be in pulverulent, liquid, or viscous form.

The generator may be of any type. It may, for example, develop a power of the order of 1 to 1000 watts.

The frequency of the generator is, in accordance with the invention, between about 10 and 2000 magahertz, for these frequencies are those which permit all of the advantages of the device according to the invention to be obtained, as will be hereinafter explained.

The frequency of the generator must be preferably equal to the resonant frequency of the resonator.

The coaxial line may be of a conventional type. Its essential purpose is to conduct the high frequency energy from the generator to the resonator according to the invention. The helical coil according to the invention is made of metallic wire and comprises a plurality of turns which are preferably wound about an axis substantially identical to that of the resonator.

The helical coil may be cylindrical in shape and have a constant or variable pitch.

It may also be non-cylindrical in shape and may be, for example, a coil with circular, elliptical, square or rectangular turns, having a variable profile and a constant or variable pitch.

The coil may also be made entirely or partially frustoconical, that is to say have dimensions and shapes which vary from turn to turn.

In one particular embodiment, the helical coil is not directly connected to the central conductor of the coaxial line. It is in this case, connected to a point on the conductive jacket by its end which is situated near the point at which the coaxial cable reaches said jacket, or by its other end or by one of its intermediate points. In this embodiment, the central conductor of the coaxial line is connected to a coupling member which consists, for example, of a coil of smaller diameter inside said helical coil.

In this embodiment the coupling member exchanges electromagnetic energy with the helical coil thus coupling the coaxial line to the resonator.

This embodiment is particularly indicated in the case in which a small load is placed inside the device, in which case the resonator containing the material to be treated reflects a relatively small inpedance to the coaxial cable of the order of the characteristic impedance of the cable.

According to another embodiment, which is more particularly indicated under contrary conditions, that is to say when the load is large, it is possible to directly connect one end of the helical coil to the central conductor of the coaxial cable.

In this case it may be advantageous to provide a connecting member at the end of the coaxial cable which is to be connected to the jacket, which connecting member is trumpet-shaped so as to permit easier matching of the impedance of the resonator containing the product to be treated to the characteristic impedance of the coaxial line.

One of the principal characteristics of the invention resides in the fact that the resonator provided with its helical coil and containing the product to be treated is matched to the input line carrying the high frequency energy, as well as to the generator. In accordance with the invention this matching is facilitated by utilizing an appropriate shape, appropriate dimensions, and an appropriate number of turns for the helical coil.

This produces a resonator having a resonant frequency between 10 and 2000 megahertz and the outer dimensions of which remain relatively small, said dimensions ranging from several millimeters to several tens of centimeters.

Moreover the apparatus according to the invention has the advantage that the matching of the resonator to the input line and the generator is relatively insensitive to variations in the load, that is to say variations in the mass and physical properties of the material which is introduced into the resonator.

This characteristic makes it possible to tolerate the variations in load which are inevitable in practice while maintaining an exceptionally high efficiency, which means a small or negligible percentage of stationary waves in the coaxial cable.

Equally good results cannot be obtained with resonant cavities of any other type, especially within the range of frequencies in question.

In a general way, when this application refers to the matching of the resonator, it should be understood that this is not a rigorously defined state, but a state which approximates the one in which the percentage of stationary waves formed in the high frequency input line remains at a value less than a few units, two or three for example.

In other words, it is considered that matching in the sense of the present application exists when the greater part of the energy of the generator is effectively dissipated in the resonator (for example more than 70%), and that matching is accomplished even when stationary waves are produced in the input line, provided that these stationary waves do not have a substantial adverse effect on the process according to the invention.

The jacket of the resonator according to the invention may, in principle, be of any shape. It may, for example, be a circular cylinder but the shape of the helical coil may be appropriately modified, so as to be cubical, or parallelopipedic, or more or less flattened.

The shape of the helical coil and the shape of the jacket constituting the resonator are chosen in each case in dependence on the material to be treated so as to permit the passage or the holding of this material near the outer surface of the helical coil in the area in which the maximum high frequency electromagnetic energy is developed inside the jacket.

It is in fact remarkable that, as a consequence of the device according to the invention, it is possible, on the one hand, to select the volume of the jacket in dependence on the dimensions of the material to be treated and, on the other hand, because of the presence of the helical coil which assists in the matching of the resonator, a sufficiently high density of electromagnetic energy is obtained in the space between the exterior of the coil and the inner surface of the jacket wall.

In this manner it is possible to obtain, with relatively low input energy, high frequency electromagnetic fields characterized by a high density of energy. This is one of the valuable advantages resulting from the device according to the invention.

It is a further object of the present invention to provide a process for creating a high frequency electromagnetic field inside a material characterized by the fact that the material is positioned or caused to circulate inside the device which has just been described in the space between the outside of the helical coil and the inner surface of the jacket wall.

The present invention also relates to another device which permits the dissipation of high frequency electromagnetic energy inside any selected material.

Another object of the present invention is accordingly to provide a new article of manufacture which consists of a device for dissipating high frequency electromagnetic energy inside a material to the surface of which the device is applied, said device being essentially characterized by the fact that it comprises in combination a conductive jacket which is closed or substantially closed in the electromagnetic sense of the term, except for a radiating opening which will be hereinafter defined; a coaxial cable connecting the jacket to a high frequency electrical generator operating at a frequency between about 10 and 2000 megahertz; said jacket comprising substantially opposite its connection to the coaxial cable an opening through which electromagnetic energy may escape to the outside; a helical coil inside the jacket transmitting the electromagnetic energy supplied by the coaxial cable, the axis of said helical coil being substantially the same as the axis of the jacket, and its end remote from the coaxial cable leading to the vicinity of the opening in said jacket, the assembly constituted by the jacket, the helical coil, and the material within which the high frequency electromagnetic energy is discharged by applying it to the opening in the jacket being matched to the input line and the high frequency generator.

The jacket according to the invention may advantageously be made of metal. According to one particular embodiment it is cylindrical in shape, but it may have a section which is circular, square, or rectangular in dependence upon the particular application. In one particular embodiment the opening in the jacket is in the form of a right section through said jacket when the latter has a cylindrical shape.

In this embodiment, the coaxial cable which conducts the high frequency energy is connected to the jacket on the side remote from the opening.

Preferably, the helical coil has circular turns but it may also have turns having a square, rectangular or elliptical section. The turns of the coil may have a constant pitch or different pitches. It is also possible to make coils having varying dimensions and shapes.

In accordance with a preferred embodiment of the invention, the end of the coil which is directed toward the opening in the jacket carries a conductive plate fixed thereto and parallel to the surface of the opening to permit a better distribution of the high frequency energy radiated against the material to be treated.

In a variation, the plate may be replaced by a sort of multi-branched antenna, the branches of which form a cone, the summit of which is positioned at the free end of the helical coil.

When it is desired to concentrate the high frequency energy near a point, it is possible to arrange for the helical coil to terminate in a point directed toward the opening of the jacket, preferably in the middle thereof, and lying on the axis of the coil.

In a preferred embodiment of the invention the coil is directly connected to the central conductor of the coaxial cable. In a variation, the helical coil is not connected to the central conductor of the coaxial cable, but the device comprises a coupling member preferably consisting of a smaller helical coil connected to the central conductor of the coaxial cable and electromagnetically coupled to the main helical coil.

The device which has just been described constitutes a partially closed resonator which, in most cases, still has a sufficiently well defined resonant frequency. It is therefore indicated that a generator should be used which corresponds to the resonant frequency of the device.

The matching of the device to the input line and the high frequency generator may be carried out by modifying the dimensions, shape and number of turns of the helical coil.

Of course this matching must correspond to the conditions of use, that is to say the conditions under which the product to be treated is positioned across the opening in the jacket.

It is a further object of the present invention to provide a new process for dissipating high frequency electromagnetic energy inside a material characterized by the fact that the opening of the device which has just been described is applied to the surface of said material.

The present invention permits an input of electromagnetic energy which is sufficiently localized to the areas which are to be treated. This method produces, among others, a heating which may be substantial and which may take place either on surfaces of relatively large dimension, or over very small areas.

The electromagnetic energy may thus be distributed over a surface of several square decimeters or concentrated on the surface of the order of several square millimeters, which would produce a particularly intense local heating.

In a variation, the device having a semi-open resonator which has just been described may also be used by placing the material to be treated against the opening as has already been described and, (when the material to be treated is thin) by placing an electrically conductive plate on the other side of the material. In this case the process is similar, in principle to the first embodiment, in which the material to be treated is placed inside the resonator.

The second embodiment which has just been described may be utilized as a simple and economical means for producing an increase in the local temperature of the epidermis. This application may be particularly useful in order to cause its penetration by creams or other treating or beauty products which are placed on the skin.

The devices according to the invention make it possible to dissipate the electromagnetic energy inside the material. It is thus possible to cause heating, and more generally, treating, as a consequence of the dissipation of energy by the dielectric effect inside the material. However, when the treatment is applied to magnetic materials, it is possible to produce heating by magnetic loss. This is particularly the case when ferrites or other similar materials are treated.

The resonators used in accordance with the invention have an outer jacket which may be made of a metallic conductor of electricity, or of a synthetic material covered with an electrically conductive layer having a thickness of from several hundredths of a millimeter up to about 1 or 2 tenths of a millimeter, depending on whether the frequency used is nearer 1000 megahertz or several tens of megahertz.

The insulating parts of the resonator inside the jacket may advantageously be made of materials such as polytetrafluroethylene which do not undergo any substantial increases in temperature when they are subjected to the action of a high frequency electric field.

In accordance with the invention it is also possible to position inside the resonator a material in which the dielectric loss factor increases with temperature. In this way the consumption of energy may be kept constant or substantially constant when the material which is being treated inside the device according to the invention is subjected to drying and requires for this purpose a consumption of energy which decreases to the extent that it dries.

Such materials in which the dielectric loss factor increases with temperature include superpolyamides such as those sold under the mark NYLON ZYTEL 101 or NYLON ZYTEL 142 by E. I. Dupont de Nemours.

It is a further object of the present invention to provide for automatic or semi-automatic matching of the device for utilizing electromagnetic energy which has just been described to the high frequency input line and generator.

This process is essentially characterized by the fact that an input signal is derived as a function of the output of the high frequency generator or the ratio (that is to say the importance) of the stationary waves at a point on the coaxial cable positioned near the apparatus, and this information is used to control the coupling between the generator and the coaxial line or the coaxial line and the resonator so as to obtain the best possible transfer of electromagnetic energy, that is to say that the generator furnishes only power which is effectively dissipated in the load connected to its output without substantial exchanges of reactive energy between the generator and the load, and this relationship is maintained independently of possible variations in the mass or physical properties of the material to be treated.

In a first method of carrying out the invention an electrical voltage is derived which is a function of the current supplied by the generator and this is used to control a motor which acts on a component of the circuit coupling the generator to the coaxial cable, for example on a condenser, in order to place this component in the position which corresponds to the best energy transfer in the sense above specified.

In another embodiment, an electrical voltage is used which is derived from the percentage of stationary waves in the coaxial cable near the device so as to automatically vary the impedance reflected by the device to the terminals of the coaxial cable, either by adjusting the coupling between the device and the coaxial cable or by adjusting an additional adjustable impedance connected in series or in parallel to the input of the resonator.

It is a further object of the present invention to provide a new article of manufacture which consists of an automatic impedance matcher oprating in accordance with the above-defined process. This device is essentially characterized by the fact that it comprises a lamp having an incandescent filament connected to the terminals of a resistance through which the anode current supplied by the high frequency generator passes, said lamp exciting a photo-electric cell the amplified current of which controls a relay which actuates a motor which drives adjusting means such as a variable condenser forming part of the circuit coupling the generator to the coaxial cable, the assembly of these components being such that the motor constantly positions the adjusting means in a position which corresponds to optimum conditions for the transfer of energy, in the sense specified above.

In order that the invention may be better understood several embodiments thereof will now be described, purely by way of illustration and example, with reference to the accompanying drawings on which:

FIG. 2 is a sectional view taken along the line II—II of FIG. 1;

FIG. 3 is a schematic sectional view taken through another embodiment of the invention;

Figure 10:
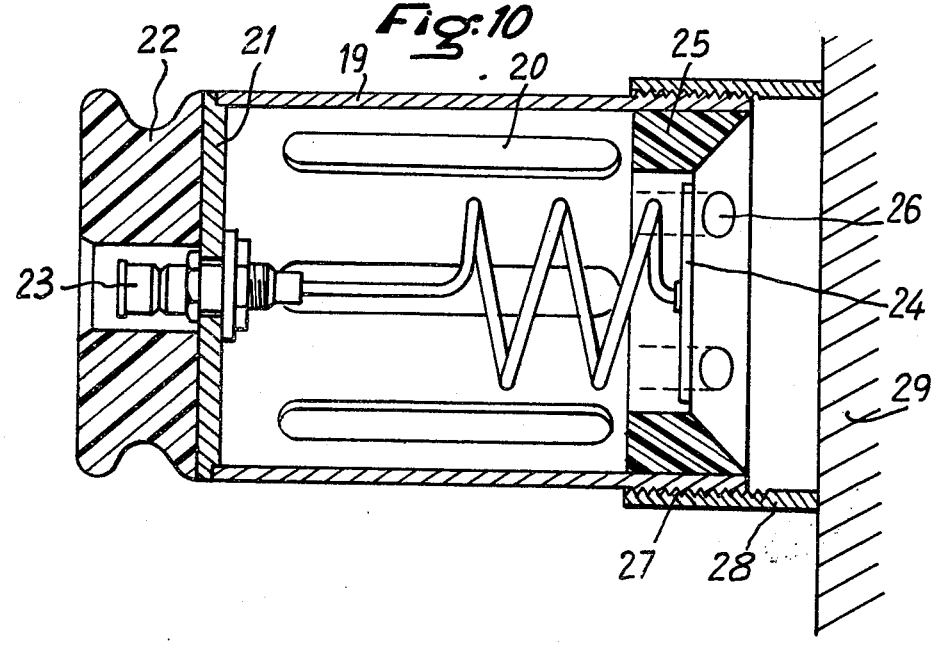

FIGS. 4–9 schematically illustrate various embodiments of the helical coil according to the invention;

FIG. 10 schematically illustrates a section through an embodiment of a device having a semi-open cavity according to the invention;

FIGS. 11, 12 and 13 schematically illustrate variations of the embodiment of FIG. 10; and FIG. 14 is a circuit diagram of the device for automatically regulating the matching of the generator to the coaxial cable and the resonator.

Figure 1A:
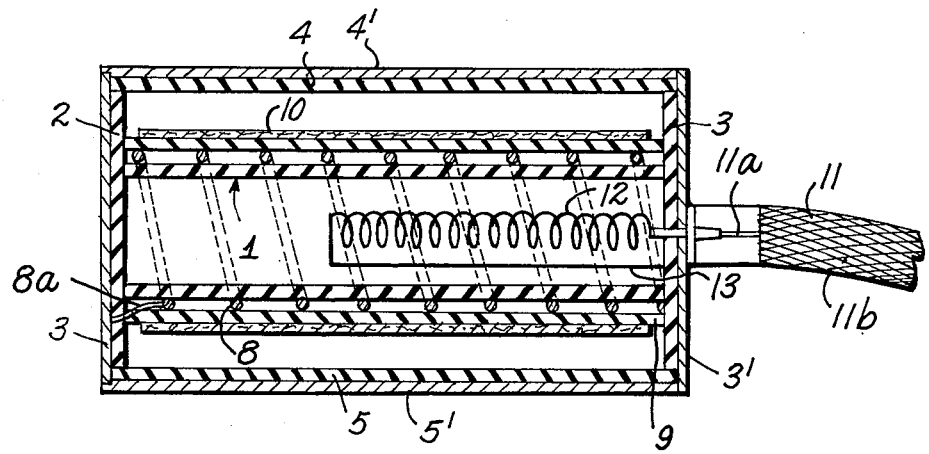
FIG. 1 is a sectional view taken along the line I-I of FIG. 2 through a first embodiment of the device according to the invention.

FIGS. 1 and 2 show a device according to the invention which is adapted to dissipate high frequency electromagnetic energy in a material which continuously circulates through the apparatus in strip form. This material may be of various kinds. It may, for example, be a product which is to be dried to a predetermined extent.

The device comprises a central core 1 made, for example, of polytetrafluroethylene. This central core carries at its ends two end members 2 and 3 of greater diameter. The end members 2 and 3 may be metallic, or may be of a synthetic material such as polytetrafluroethylene and externally coated with a metallic layer which is electrically conductive.

A chamber defined by two jacket halves 4 and 5 (FIG. 2), pivotally connected at 6, constitutes the principal part of the resonator according to the invention. The halves 4 and 5 are adapted to fit around the peripheries of the end members 2 and 3. The end members 2 and 3 carry a stationary member 7 the utility of which will be hereinafter explained. The two halves 4 and 5, as well as the stationary member 6, may advantageously be made of a metal such as aluminum.

The halves 4 and 5 may be provided, if desired, with small openings permitting the elimination of humidity released inside the resonator during the treatment in accordance with the invention.

As may be seen in FIG. 1, the regular helical coil 8 is mounted on the core 1. One end of this coil is electrically connected to the conductive part of the jacket. The coil 8 is encircled by a cylinder 9, made of polytetrafluroethylene, for example. This cylinder defines the surface on which the product to be treated 10 slides. As has already been explained, this product may take the form of a relatively thin strip.

FIG. 1 also shows the coaxial cable 11, the central conductor 11a of which leads to a coupling member 12 which, in this case, is a helical coil having a small diameter coaxially positioned inside the helical coil 8. The end of the helical coil 12 is connected to ground by the wire 13. As may be seen on FIG. 2, the rotating cylinders 14, which bear against the strip of material 10 which is to be treated, hold said strip against almost the entire periphery of the cylindrical member 9.

The metallic part 7 is intended to prevent any substantial portion of the electromagnetic energy developed inside the resonator from being radiated to the exterior thereof.

It will be appreciated from what has been said that, by separating the two halves 4 and 5 and causing them to pivot about the axis 6, it is possible to easily place the product to be treated inside the jacket, after which it is driven at a speed which is dependent on the nature of the treatment which is to be applied thereto, so as to cause it to remain inside the cavity for the desired time.

In accordance with the invention the coaxial cable 11 is connected to a high frequency generator operating at a frequency between about 10 and about 2000 megahertz.

The characteristics of the helical coil 8 (e.g., the number of turns, diameter of turns, etc.), as well as the characteristics of the coupling member 12, are so selected that when the product 10 which is to be treated is inside the resonator, the resonator is matched to the impedance of the line 11. A generator is selected having a frequency which corresponds to the resonant frequency of the cavity.

FIG. 3 schematically illustrates a variation of the embodiment which is illustrated on FIGS. 1 and 2. This variation relates to a device adapted to continuously treat a liquid which is introduced thereinto.

FIG. 3 shows the helical coil 8 which, in this variation, is directly connected to the central conductor 11a of the coaxial cable 11. FIG. 3 also shows the cylinder 9 made of polytetrafluroethylene, for example, and which encircles the helical coil 8.

In this case the conductive jacket may advantageously consist of a polytetrafluroethylene cylinder 15 connecting, as in the preceeding embodiment, the two end members 2 and 3. The cylinder 15 and the end members 2 and 3 are metallized in order to render them conductive.

Two tubes 16 and 17 permit the entry and evacuation of the liquid which is to be treated in accordance with the invention. FIG. 3 also shows how the sheath 11b of the coaxial cable 11 is connected to a conductor 18 which is trumpetshaped and connected to the end member 3. This makes it easier to match the impedance of the line 11 to the resonator according to the invention.

Figure 4:
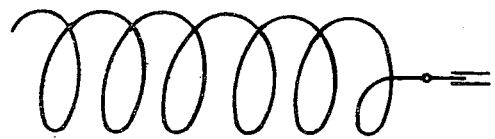
Figure 5:
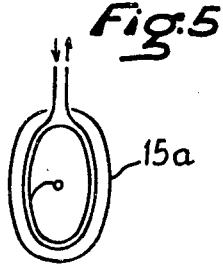

FIGS. 4 and 5 show another embodiment of the helical coil which has turns having a variable pitch as may be seen in FIG. 4, and the section of which is elliptical as may be seen in FIG. 5. FIG. 5 also schematically shows how this elliptical form facilitates the sliding movement of the product to be treated, the direction of movement of which is indicated by arrows.

Figure 6:
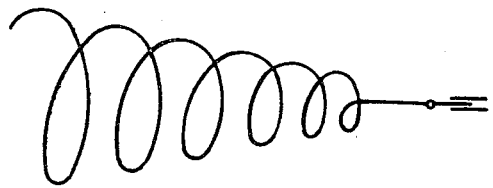
Figure 7:
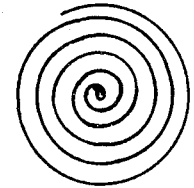
Figure 8:
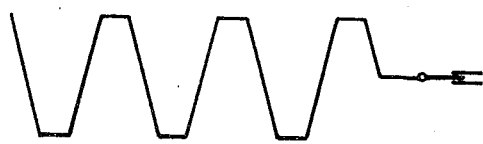
Figure 9:
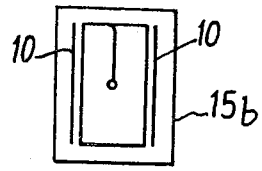

FIGS. 6 and 7 show an embodiment of the helical coil having turns of decreasing diameter. FIGS. 8 and 9 show the case in which the helical coil consists of turns having a rectangular section.

As may be seen in FIG. 9, the jacket 15b also has a parallelopipedic form adapted to the shape of the coil. In this case, the product to be treated, which is in the form of a sheet 10, may be moved parallel to the axis of the helical coil.

FIG. 10 schematically represents another embodiment of the device according to the invention. This embodiment uses a semi-open cavity.

FIG. 10 shows an electrically conductive cylinder (of metal for example) 19, which is provided with oblong openings 20. The left end of this cylinder is connected to a metallic end member 21 on which is mounted a member 22 of a synthetic material which serves as a handle for the device according to the invention. This member 22 has a central orifice which permits the coaxial cable to be connected to the input terminal 23. This terminal 23 is itself connected to the helical coil 8 which in the present case, comprises three turns and terminates in a flat plate 24 perpendicular to the axis of the helical coil 8.

To hold the coil and the disc 24 in position a member 25 of polytetrafluroethylene is positioned inside the cylinder 19 and is provided with openings 26 to permit the circulation of air.

The right side of the cylindrical jacket 19 is provided with threads 27 on which is mounted a threaded ring 28 which is adapted to be applied to the surface of the material 29 which is to be treated. It will be noted that, by turning the ring 28 with respect to the cylinder 19, it is possible to vary the distance between the material 29 to be treated and the disc 24.

The embodiment which has just been described may be used, for example, to apply local heat to the skin, which then constitutes the material 29.

The heating which accompanies a treatment by high frequency energy may be used to insure better penetration of products such as lotions, creams and unguents which are applied to the skin.

In a particular embodiment the helical coil 8, which comprises three turns, has a diameter of 16 millimeters and a pitch of 8 millimeters. The disc 24 has a diameter of 20 millimeters. The jacket of the resonator has a length of 42 millimeters and a diameter of 32 millimeters. Excellent results are obtained by supplying this device with electromagnetic energy at a frequency of 327 megahertz.

FIGS. 11, 12 and 13 show specific embodiments of this device. FIG. 11 schematically illustrates a helical coil 8 which terminates in a plate 24 positioned parallel to the material 29 which is to be treated. In this case the central conductor 11a of the coaxial cable is directly connected to the helical coil 8.

In the variation illustrated on FIG. 12, the helical coil 8 terminates in an antenna having several branches 24a, while the central conductor 11a of the coaxial cable terminates at a coupling member consisting of a small helical coil 12.

FIG. 13 schematically illustrates a variation in which the helical coil 8 terminates in a point 24b adapted to concentrate the electromagnetic energy in the zone 29a of the material 29 to be treated. In this case, the helical coil 8 is directly connected to the central conductor of the coaxial cable.

Of course the embodiments of the various components which have just been described are given purely be way of illustration. These different embodiments may be combined and the examples which have been given are intended solely in order to illustrate the diversity of possibilities. In order that the invention may be better understood the characteristics of three representative embodiments of the semi-open resonator according to the invention will now be described, purely by way of example. These three embodiments comprise cylindrical jackets and helical coils having circular turns and a constant pitch. It is obvious, however, that the invention is not limited to such shapes and such characteristics of the jacket and coil.

EXAMPLE 1

The jacket has a diameter of 1.25 centimeters and a length of 1.5 centimeters. This cylindrical jacket is open at one of its end, and contains a helical coil extending along its axis having nine turns at a constant pitch of 0.1 centimeters, with a diameter of 0.68 centimeters. This device may be supplied with a current having a frequency of 400 megahertz.

EXAMPLE 2

A jacket is used having a diameter of 5 millimeters and a height of 7 millimeters. The jacket is open at one end. The helical coil consists of 24 turns having a diameter of 2.7 millimeters and a pitch of 0.17 millimeters. This device may be supplied with a current having a frequency of 400 megahertz. It permits a concentration of electromagnetic energy in a very restricted area, with a high concentration of energy.

EXAMPLE 3

A device having a semi-open cavity according to the invention which has relatively large dimensions consists of a jacket having a diameter of 44 centimeters and a length of 41 centimeters, and provided with an opening at one end. The helical coil consists of three turns 24 centimeters in diameter, having a pitch of 6.2 centimeters. This device may be supplied by a current having a frequency of 40 megahertz.

FIG. 14 shows an embodiment of the device permitting automatic matching of the generator to the line which supplies the high frequency energy to the resonator according to the invention.

FIG. 14 schematically shows the device 30 according to the invention, as well as a cable 31 which supplies it and which leads at its other end through a secondary transformer coil 32 and a variable condenser 33 to the output circuit 34 of the generator, which is not shown.

The output circuit 34 also comprises a primary transformer coil 35 which insures the transmission of energy to the cable 31.

In accordance with one embodiment of the invention an electrical resistance 36 may be placed in series with the output circuit 34 and an incandescent lamp is connected across the terminals of the resistance.

The characteristics of the resistance 36 and the lamp 37 are so selected that when the current in the output circuit 34 is at its maximum, the voltage difference across the terminal of the resistance 36 results in a maximum luminous intensity in the lamp 37.

the contrary, when the current in the output circuit. 34 decreases, the intensity of the light radiated by the lamp decreases rapidly.

In accordance with the invention, the lamp 37 is positioned in front of a photo-electric cell 38 which, through an amplifier circuit, controls a bistable relay 39.

The bistable relay 39 determines whether a motor 40 which turns the variable condensor 33 is supplied or is not supplied.

In one particular embodiment the current amplifier of the photo-electric cell 38 consists of two transistors 41 of the NPN type such as sold under the number 2N2905 by the RTC Company, and by two resistances 42 and 43.

In this particular embodiment the resistance 42 has a adjustable value between 30 and 50 kilohms, as a function of the characteristics of the lamp 37. The resistance 43 has a value of 2 kilohms.

In the embodiment described, the photo-electric cell 38 is a cell sold under the number OAP12 by the RTC Company.

The relay 39 is a relay operating for example on five volts and 40 milliamperes.

The electric motor 40 is a micromotor operating on alternating current having a power of two watts. It drives the condenser 33 at a speed of ten revolutions a minute and because of its symmetry the condenser passes twice during each revolutions through the same capacitative value.

The operation of the device is as follows: If it be supposed that, in the initial state, the flow of current through the output circuit 34 is then sufficient to light the lamp 37, no current is amplified by the amplifier and the relay 39 is placed in a position which closes the supply circuit of the micromotor 40. The micromotor 40 turns the condenser 33 and for a certain position of the latter, matching is produced and the current supplied in the output circuit 34 becomes normal. The lamp 37 then acts rapidly on the cell 38, the amplified current of which operates the relay 39 and stops the motor, which stops the condenser 33 in the matching position.

When something occurs which impairs the matching, the lamp 37 goes out and the process recommences.

It will be seen that, as a consequence, a relatively simple and automatic matching of the generator to the coaxial line is obtained. It will be noted that, at the rate of 10 turns per minute and two matching positions per turn, it requires at most three seconds to reach a matching position of the condenser 33.

It will, of course, be appreciated that the embodiments which have been described have been given purely by way of illustration and example and may be modified as to detail without thereby departing from the basic principles of the invention.

What is claimed is:

1. Device for dissipating high frequency electromagnetic energy from a high frequency electromagnetic generator operating at between about 10 and about 2000 megahertz inside a material which device comprises in combination:
    an elongated cavity resonator comprising an electrically conductive substantially closed outer jacket,
    an electrically conductive helical coil and means coaxially locating said helical coil inside said outer jacket, in a position spaced inwardly from the inner wall of said jacket,
    electrically insulating means for locating the material to be treated between the wall of said jacket and said helical coil,
    a coaxial line adapted to be connected at one end to said generator and comprising an external conductor connected at the other end of said line to said jacket, and a central conductor,
    coupling means for transferring energy from the central conductor to said helical coil and for radiating energy inside said jacket for dissipation inside said material to be treated,
    the total impedance presented by said resonator and said material to be treated being matched to that of the coaxial line and the high frequency generator.

2. Device as claimed in claim 1 in which the electrically conductive jacket is made of an insulating material having a low dielectric loss factor covered with a coating of an electrically conductive material.

3. Device as claimed in claim 1 in which the jacket has openings therein large enough to permit the passage therethrough of material to be treated but too small to permit substantial diffusion of the electromagnetic energy outside the device.

4. Device as claimed in claim 1 in which the frequency of the generator is substantially equal to the resonant frequency of the resonator.

5. Device as claimed in claim 1 in which the helical coil is circular in cross-section.

6. Device as claimed in claim 1 in which the coaxial input line has a central conductor connected to a primary coil located inside said helical coil and transferring energy to said helical coil, which acts as a secondary coil.

7. Device as claimed in claim 6 in which the helical coil is electrically connected to the conductive jacket.

8. Device as claimed in claim 1 in which said jacket contains outside the helical coil a material having a coefficient of dielectric loss which increases with an increase in temperature.

9. Device as claimed in claim 1 in which the jacket comprises two end members and two jacket halves pivotally connected to each other and adapted to fit around the peripheries of said end members.

10. Device as claimed in claim 1 in which said means for locating said material to be treated comprises a support made of an insulating material having only a small dielectric loss factor.

11. Device as claimed in claim 1 in which said helical coil is electrically connected to said outer jacket.

12. A method of creating a high frequency electrical field inside a material comprising, in combination, the steps of: providing an elongated cavity resonator comprising an electrically conductive substantially closed outer jacket and a helical coil coaxially located within and spaced inwardly from the inner wall of said jacket, locating the material to be treated inside the jacket but outside said coil, supplying electromagnetic waves at a frequency of between about 10 and about 2000 megahertz to said resonator from a high frequency electromagnetic source through a coaxial transmission line for radiation inside said jacket, and matching the total impedance presented by the jacket, the coil, and the material to be treated with the impedance of the transmission line and the high frequency source.

13. Device for dissipating inside a material high frequency electromagnetic energy supplied through a coaxial line having a central conductor from a high frequency electromagnetic generator, which device comprises in combination:
    an elongated cavity resonator comprising an electrically conductive, substantially closed, outer jacket having end walls and at least one side wall,
    an electrically conductive helical coil located inside said outer jacket in a position spaced inwardly from the inner surface of said at least one side wall,
    electrically insulating means for locating the material to be treated between said at least one side wall of said jacket and said helical coil, and
    coupling means for introducing energy from said central conductor into said jacket for dissipation inside the material being treated,
    the electrical parameters of said coil and coupling means being so selected that the total impedance of said resonator, when it contains said material to be treated, is matched to the total impedance of said coaxial line and said generator.

14. Device for dissipating high frequency electromagnetic energy inside a material, which device comprises:
    an elongated cavity resonator comprising an electrically conductive, substantially closed, outer jacket having end walls, at least one side wall, and at least one narrow opening for admitting said material, an electrically conductive helical coil located inside said outer jacket in a position spaced inwardly from the inner surface of said at least one side wall, electrically insulating means for supporting the material to be treated spaced from said helical coil between said helical coil and said at least one side wall, and coupling means for introducing electrical energy supplied to said coupling member into said jacket for dissipation within said material, said coupling means and helical coil constituting impedance means for increasing the effective impedance of said cavity and bringing its resonant frequency, when supplied with said material, to a selected value between 10 and 2000 megahertz.

* * * * *

UNITED STATES PATENT OFFICE
CERTIFICATE OF CORRECTION

PATENT NO. : 3,980,855
DATED : September 14, 1976
INVENTOR(S) : Georges Boudouris et al It is certified that error appears in the above-identified patent and that said Letters Patent are hereby corrected as shown below:

The term of this patent subsequent to February 4, 1992 has been disclaimed.

Signed and Sealed this

Seventh Day of December 1976

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,980,855
DATED : September 14, 1976
INVENTOR(S) : GEORGES BOUDOURIS et al It is certified that error appears in the above-identified patent and that said Letters Patent are hereby corrected as shown below:

[30] Foreign Application Priority Data

March 27, 1972.......Luxembourg......... 65,047

Signed and Sealed this

First Day of February 1977

[SEAL]

Attest:

RUTH C. MASON
Attesting Officer

C. MARSHALL DANN
Commissioner of Patents and Trademarks